(12) United States Patent
Sipinski et al.

(10) Patent No.: US 7,455,245 B2
(45) Date of Patent: Nov. 25, 2008

(54) DIFFUSION DEVICE

(75) Inventors: Gene Sipinski, Elgin, IL (US); Jeffrey L. Harwig, New Berlin, WI (US); Murthy S. Munagavalasa, Racine, WI (US); Gopal P. Ananth, Racine, WI (US)

(73) Assignee: S.C. Johnson & Son, Inc., Racine, WI (US)

( * ) Notice: Subject to any disclaimer, the term of this patent is extended or adjusted under 35 U.S.C. 154(b) by 34 days.

(21) Appl. No.: 11/457,728

(22) Filed: Jul. 14, 2006

(65) Prior Publication Data

US 2008/0011875 A1    Jan. 17, 2008

(51) Int. Cl.
*B05B 1/08* (2006.01)
*B05B 9/00* (2006.01)

(52) U.S. Cl. .................... 239/102.2; 239/70; 239/71; 239/326

(58) Field of Classification Search ............. 239/102.2, 239/71, 326, 4, 44, 239, 70, 102.1, 145, 302, 239/338, 533.13, 533.14
See application file for complete search history.

(56) References Cited

U.S. PATENT DOCUMENTS

| | | |
|---|---|---|
| 6,293,474 B1 | 9/2001 | Helf et al. |
| 6,296,196 B1 | 10/2001 | Denen et al. |
| 6,341,732 B1 | 1/2002 | Martin et al. |
| 6,378,780 B1 | 4/2002 | Martens, III et al. |
| 6,382,522 B2 | 5/2002 | Tomkins et al. |
| 6,386,462 B1 | 5/2002 | Martens, III |
| 6,439,474 B2 | 8/2002 | Denen |
| 6,446,880 B1 | 9/2002 | Schram et al. |
| 6,450,419 B1 | 9/2002 | Martens, III et al. |
| 6,482,863 B2 | 11/2002 | Munagavalasa et al. |
| 6,486,726 B1 | 11/2002 | Worley, Sr. et al. |
| 6,706,988 B1 | 3/2004 | Helf et al. |
| 6,752,327 B2 | 6/2004 | Martens, III et al. |
| 6,789,741 B2 | 9/2004 | Varanasi et al. |
| 6,793,149 B2 | 9/2004 | Schramm et al. |

(Continued)

FOREIGN PATENT DOCUMENTS

AU    199664444    3/1997

(Continued)

OTHER PUBLICATIONS

PCT/US2007/015932 International Search Report and Written Opinion dated Dec. 18, 2007.

(Continued)

*Primary Examiner*—Darren W Gorman

(57) ABSTRACT

A diffusion device includes a housing having a battery disposed therein and adapted to receive a replaceable fluid reservoir for holding a fluid, wherein the fluid reservoir includes a wick for movement of the fluid to a discharge end thereof. The diffusion device further includes a piezoelectric element energized by a power source for vibrating a perforated orifice plate disposed adjacent the discharge end of the wick, wherein the piezoelectric element develops vibratory movement to pump the fluid from the discharge end through the perforated discharge plate and into the atmosphere. A control circuit and light emitting diode ("LED") are disposed in the housing, wherein the control circuit energizes the LED at a particular frequency when the dispenser is active and a voltage developed by the battery is above a threshold voltage.

19 Claims, 10 Drawing Sheets

U.S. PATENT DOCUMENTS

| | | | |
|---|---|---|---|
| 6,843,430 | B2 | 1/2005 | Boticki et al. |
| 6,857,580 | B2 | 2/2005 | Walter et al. |
| 6,896,193 | B2 | 5/2005 | Helf et al. |
| 6,909,840 | B2 | 6/2005 | Harwig et al. |
| 6,969,008 | B2 | 11/2005 | Helf et al. |
| 7,017,829 | B2 | 3/2006 | Martens, III et al. |
| 7,070,121 | B2 | 7/2006 | Schramm et al. |
| 2002/0121274 | A1 | 9/2002 | Borland et al. |
| 2004/0144853 | A1 | 7/2004 | Helf et al. |
| 2005/0205916 | A1 | 9/2005 | Conway et al. |
| 2006/0120080 | A1 | 6/2006 | Sipinski et al. |
| 2006/0175426 | A1 * | 8/2006 | Schramm et al. .............. 239/69 |

FOREIGN PATENT DOCUMENTS

| | | |
|---|---|---|
| DE | 4328959 | 3/1995 |
| EP | 897 755 | 2/1999 |
| EP | 1 475 108 | 11/2004 |
| JP | 57042603 | 3/1982 |
| JP | 7196418 | 8/1995 |
| JP | 09-201155 A | 8/1997 |
| NL | 19991012690 | 7/2000 |
| WO | WO 93/10910 | 6/1993 |
| WO | WO 02/47482 | 6/2002 |
| WO | WO 03/068413 * | 8/2003 |
| WO | 2004010762 A2 | 5/2004 |
| WO | 2004043502 A1 | 5/2004 |
| WO | WO 2004/048002 | 6/2004 |
| WO | WO 2005/046332 | 5/2005 |
| WO | WO 2006/134353 | 12/2006 |

OTHER PUBLICATIONS

International Search Report and Written Opinion in PCT/US2007/015934 dated Mar. 7, 2008.

International Search Report and Written Opinion in PCT/US2007/015933 dated Jun. 2, 2008.

* cited by examiner

DIFFUSION DEVICE

CROSS REFERENCE TO RELATED APPLICATIONS

Not applicable

REFERENCE REGARDING FEDERALLY SPONSORED RESEARCH OR DEVELOPMENT

Not applicable

SEQUENTIAL LISTING

Not applicable

BACKGROUND OF THE INVENTION

1. Field of the Invention

The present invention elates to diffusion devices and, more particularly, to droplet delivery devices capable of dispensing droplets of a predictable size for suspension or evaporation in an ambient environment.

2. Description of the Background of the Invention

A multitude of active material diffusion devices or diffusers exist in the marketplace. Many of such devices are passive devices that require only ambient air flow to disperse the liquid active material therein. Other devices are battery-powered or receive household power via a plug. A cord may be coupled between the plug and the device, or the plug may be mounted directly on the device.

Various means for dispensing active materials from diffusion devices are also known in the art. For example, some diffusion devices include a heating element for heating an active material to promote vaporization thereof. Other diffusion devices employ a fan to generate air flow to direct active material out of the diffusion device into the surrounding environment. In another type of diffusion device, active material may be emitted from the device using a bolus generator that develops a pulse of air to eject a scent ring. Still other diffusion devices utilize an ultrasonic transducer to break up an active material into droplets that are ejected from the device.

In one example, a diffusion device includes two heaters for dispersion of fragrances. The device includes a housing, a plug extending from the housing for insertion into an outlet, and two containers having fragrances therein and wicks extending therefrom to absorb fragrances from the containers. Each of the heaters is disposed adjacent one of the wicks to heat the respective wick to vaporize the fragrances therein. Optionally, a CPU controlled by internal software may first activate a first of the two heaters for a predetermined period of time. Once the period of time expires, the CPU deactivates the first heater and thereafter activates the second heater.

Other diffusion devices include a housing having a cavity for receiving a cartridge. The cartridge has a plurality of scent elements disposed on a rotatable disk. A blower is mounted in the housing to generate airflow by passing air across a scent element and out an aperture in the housing. The housing further includes rotating means that rotate the rotatable disk, thereby rotating the scent elements thereon. The device diffuses a first scent for a predetermined time period and thereafter rotates the disk such that a second scent is disposed in the airflow and the second scent is diffused for the predetermined time period. This process repeats for the remaining scents until the last scent element is diffused for a time period and then the disk is rotated to a home position.

Vibratory-type liquid atomization devices are described in Helf et al. U.S. Pat. No. 6,293,474, Martin et al. U.S. Pat. No. 6,341,732, Tomkins et al. U.S. Pat. No. 6,382,522, Martens, III et al. U.S. Pat. No. 6,450,419, Helf et al. U.S. Pat. No. 6,706,988, and Boticki et al. U.S. Pat. No. 6,843,430, all of which are assigned to the assignee of the present application and which are hereby incorporated by reference herein. These patents disclose devices comprising a piezoelectric actuating element coupled to a liquid atomization plate. The piezoelectric actuating element vibrates the liquid atomization plate in response to alternating electrical voltages applied to the actuating element. The vibration of the plate causes atomization of a liquid supplied by a liquid delivery system. An electrical circuit is provided to supply the alternating electrical voltages to conductive elements that are in electrical contact with opposite sides of the actuating element. The conductive elements may also serve to support the actuating element and the liquid atomization plate in a housing that contains the device.

SUMMARY OF THE INVENTION

According to one aspect of the present invention, a diffusion device includes a housing having a battery disposed therein and adapted to receive a replaceable fluid reservoir for holding a fluid, wherein the fluid reservoir includes a wick for movement of the fluid to a discharge end thereof. The diffusion device further includes a piezoelectric element energized by a power source for vibrating a perforated orifice plate disposed adjacent the discharge end of the wick, wherein the piezoelectric element develops vibratory movement to pump the fluid from the discharge end through the perforated discharge plate and into the atmosphere. A control circuit and light emitting diode (LED) are disposed in the housing, wherein the control circuit energizes the LED at a particular frequency when the dispenser is active and a voltage developed by the battery is above a threshold voltage.

According to another aspect of the present invention, a diffusion device includes a housing adapted to receive a replaceable fluid reservoir for holding a fluid, wherein the fluid reservoir includes a wick for movement of the fluid to a discharge end thereof. The diffusion device further includes a piezoelectric element energized by a power source for vibrating a perforated orifice plate disposed adjacent the discharge end of the wick, wherein the piezoelectric element develops vibratory movement to pump the fluid from the discharge end through the perforated discharge plate and into the atmosphere. Still further, the diffusion device includes a control circuit and a light emitting diode ("LED") disposed in the housing and a single 1.5 volt AA battery disposed within the housing for drive the piezoelectric element and the LED. The single battery is capable of periodically operating the piezoelectric element to dispense fluid from the device for 10 hours a day for at least 45 days.

Other aspects and advantages of the present invention will become apparent upon consideration of the following detailed description.

DETAILED DESCRIPTION

Figure 1:
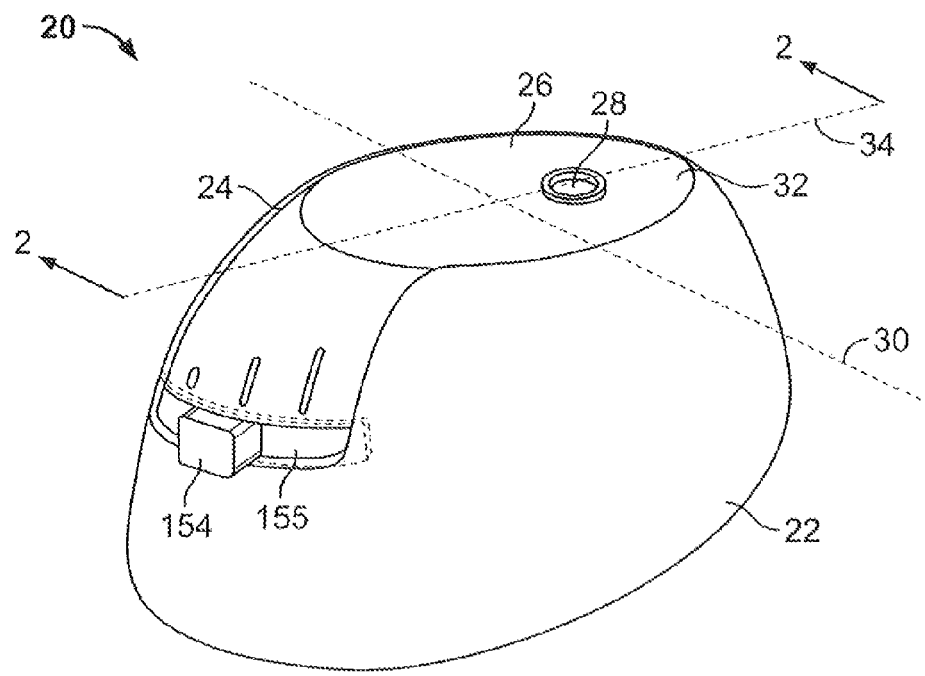
FIG. 1 is an isometric view of rear and top sides of a first embodiment of a diffusion device having a replaceable fluid reservoir inserted therein.
Figure 1A:
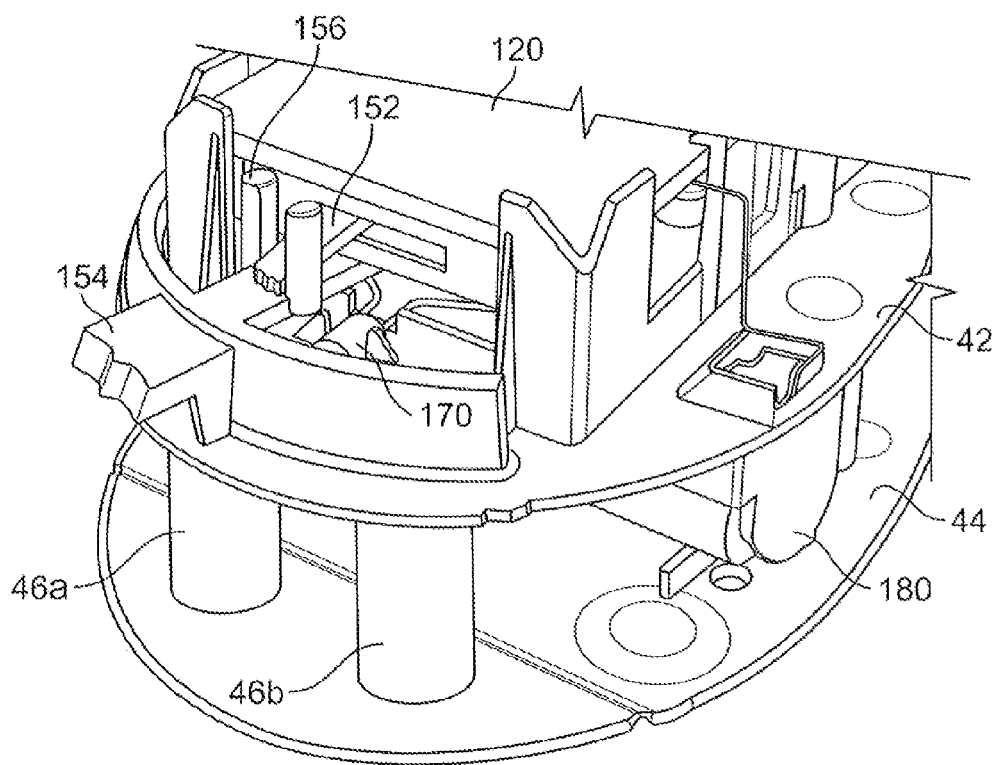
FIG. 1A is an isometric view of rear and top sides of a support chassis disposed within the diffusion device of FIG. 1.
Figure 2:
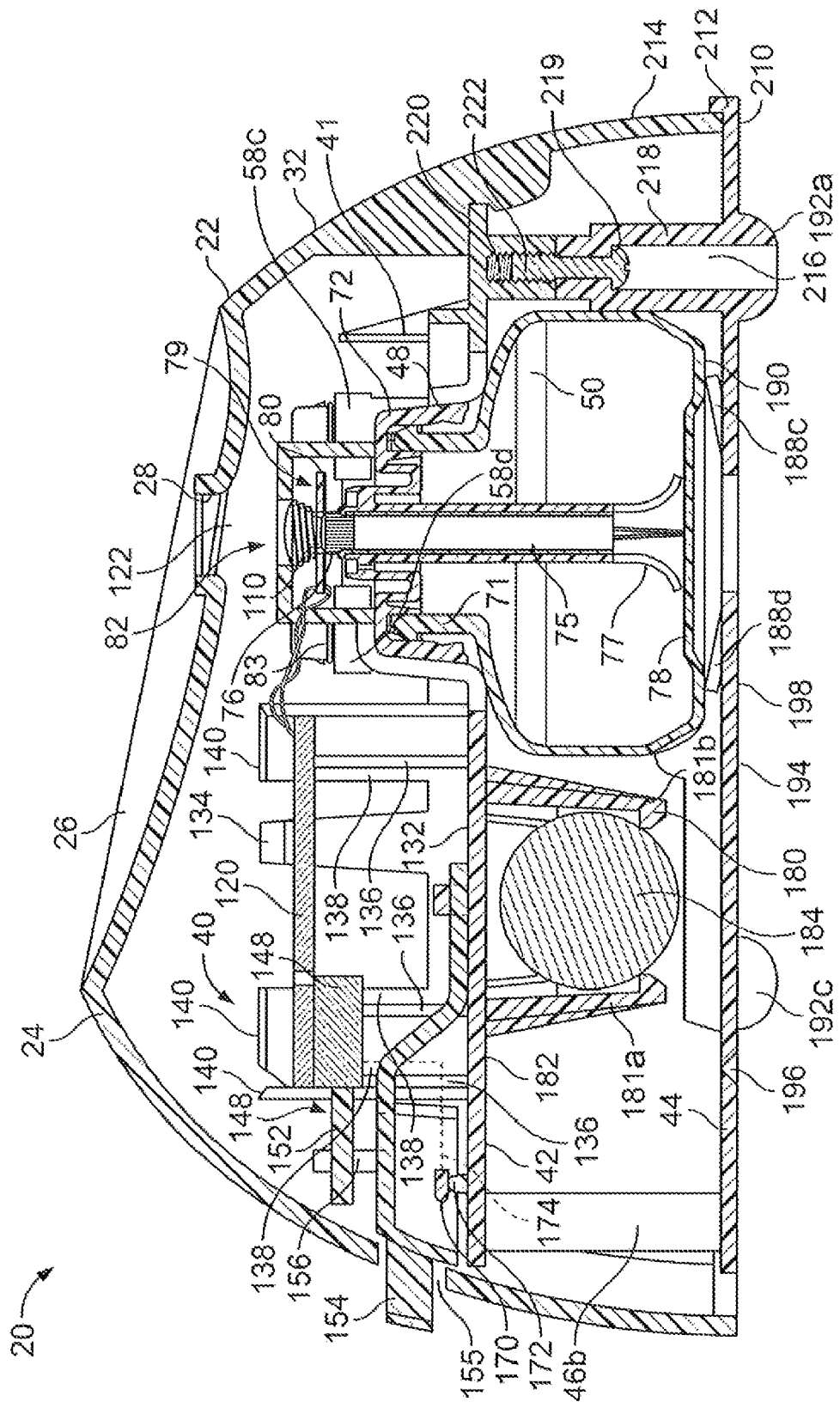
FIG. 2 is a cross sectional view taken generally along the lines 2-2 of FIG. 1.

As depicted in FIGS. 1, 1A, and 2, a diffusion device 20 includes a housing 22 with a top portion 24 having a concave depression 26. An aperture 28 extends through the housing 22 within the concave depression 26 for dispersal of an atomized liquid through the aperture 28. The aperture 28 is centered along a lateral axis 30 of the housing 22 and is offset toward a front end 32 of the housing 22 along a longitudinal axis 34 (FIG. 1).

Figure 3:
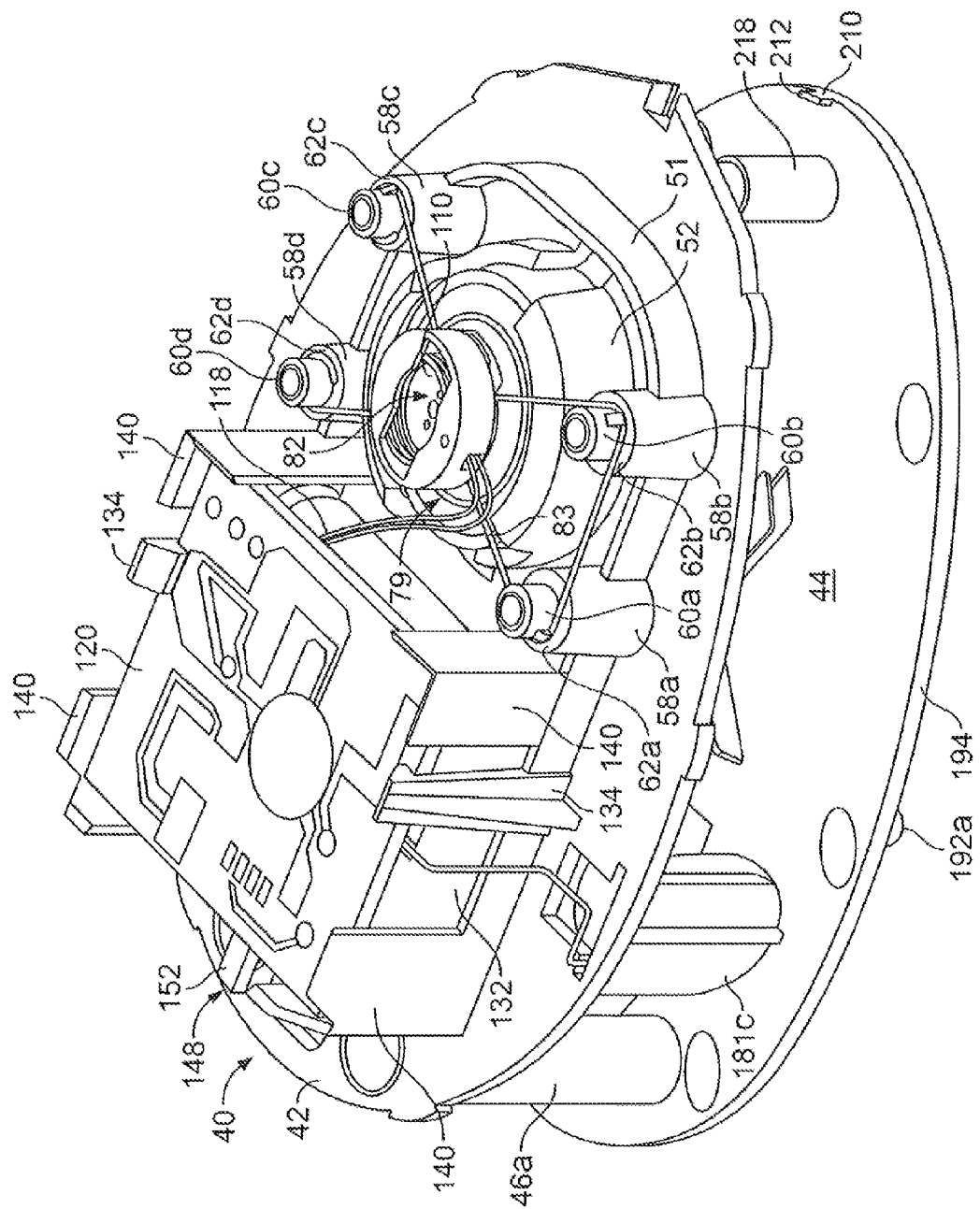
FIG. 3 is a top isometric view of the support chassis disposed within the diffusion device of FIG. 1.
Figure 4:
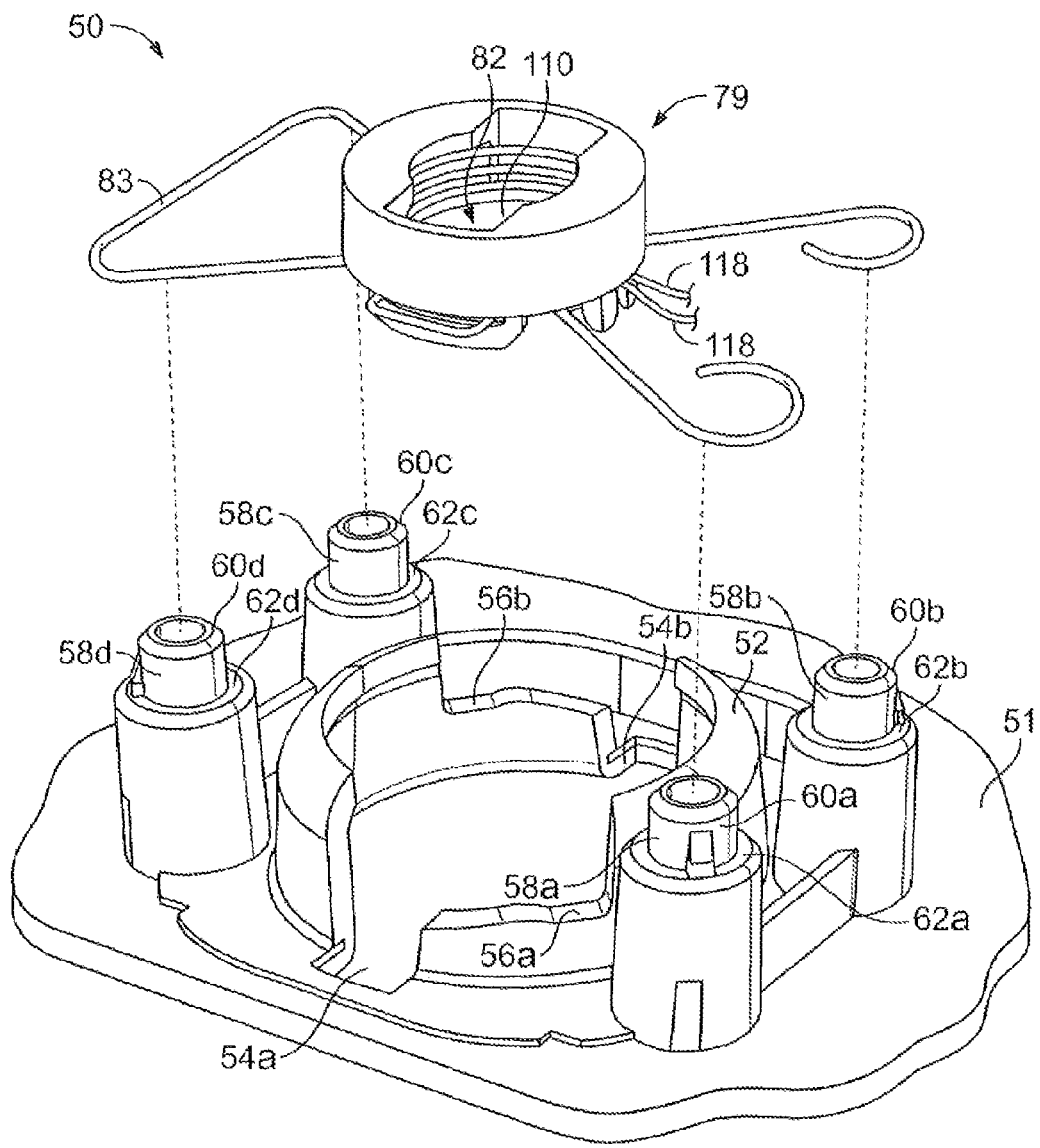
FIG. 4 is an enlarged exploded top isometric view of piezoelectric actuator assembly disposed within the support chassis of FIG. 3.
Figure 5:
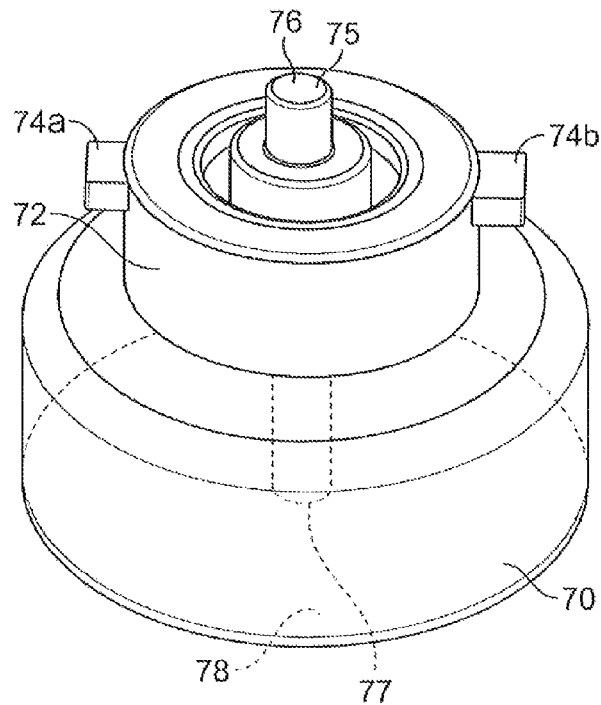
FIG. 5 is a top isometric view of a fluid reservoir for insertion into the diffusion device of FIG. 1.

Referring to FIGS. 2 and 3, the diffusion device 20 includes a support chassis 40 disposed within the housing 22. In particular, the support chassis 40 is secured within the housing 22 by an interference fit with shouldered portions of protrusions 41 on an inner surface of the housing 22. The support chassis 40 may be similar or identical to the chassis disclosed in Ganey U.S. Pat. No. 6,896,193, the disclosure of which is incorporated by reference herein. The support chassis 40 includes an upper oval-shaped base plate 42 and a lower oval-shaped base plate 44 joined to one another by first and second posts 46a, 46b. The upper base plate 42 is formed with an opening 48 (FIG. 2) therein that receives a replaceable fluid reservoir 50. As best seen in FIG. 4, a support 51 that forms a part of the upper base plate 42 includes an upwardly extending cylindrically shaped reservoir mounting wall 52. The mounting wall 52 includes two opposing bayonet slots 54a, 54b formed therein and walls 56a, 56b defining corresponding circumferentially extending detents forming a part of the bayonet slots 54a, 54b, respectively. Four cylindrical mounting posts 58a-58d extend upwardly from the support plate 51 adjacent the mounting wall 52 wherein each mounting post 58 includes a smaller projection 60a-60d extending upwardly from a top portion 62a-62d thereof. The fluid reservoir 50 is removably inserted into the diffusion device 20, as discussed in detail hereinafter. The fluid reservoir 50 includes an active material in liquid form therein, wherein the active material is preferably an insecticide, an insect repellant, or an insect attractant. Alternatively, the active material may be a fragrance, a disinfectant, a sanitizer, an air purifier, an aromatherapy scent, an antiseptic, an odor eliminator, an air-freshener, a deodorizer, or any other active ingredient(s) that are usefully dispersed into the air. Examples of preferable insecticides are Transfluthrin, Metofluthrin, Pynamin Forte, Etoc, and Vapothrin.

As shown in FIGS. 2 and 5, the fluid reservoir 50 comprises a transparent cylindrical container 70 with a neck 71 (seen in FIG. 2). A combination plug and wick holder 72 is affixed to the neck 71, wherein the plug and wick holder 72 includes a pair of laterally extending mounting lugs 74*a*, 74*b*. A wick 75 is disposed within the reservoir 50 in contact with fluid therein. An upper end 76 of the wick 75 extends beyond the neck and a lower end 77 of the wick 75 is disposed within the reservoir 50 toward a bottom surface 78 thereof. The wick 75 transfers liquid by capillary action from within the reservoir 50 to the upper end 76 of the wick 75. The fluid reservoir 50 is inserted into the support chassis 40 by aligning the lugs 74*a*, 74*b* with the bayonet slots 54*a*, 57*b*, respectively, (FIG. 4) and pushing the reservoir 50 upwardly, thereby inserting the lugs 74*a*, 74*b* into the respective bayonet slots 54*a*, 54*b*. The reservoir 50 is thereafter rotated to force the lugs 74*a*, 74*b* to engage with the walls 56*a*, 56*b* defining the detent portions of the respective bayonet slots 54*a*, 54*b* to secure the reservoir within the diffusion device 20.

Referring next to FIGS. 2-4, a piezoelectric actuator 79 includes a piezoelectric element 80 and orifice plate assembly 82 similar or identical to those described in U.S. Pat. No. 6,896,193. The actuator 79 is mounted on the mounting posts 58*a*-58*d* by a mental support wire 83 that extends through the actuator 79 and around the mounting posts 58*a*-58*d*. Referring to FIGS. 3 and 4, the orifice plate assembly 82 comprise an orifice plate 110 (FIGS. 2 and 3). An outer circumferential portion of the orifice plate 110 is in contact with the piezoelectric actuator 80. Eighty-four perforations or holes (not seen due to the scale of the drawings) of nominally equal diameter (within a tolerance range as noted in greater detail hereinafter) extend through the orifice plate 110. In the preferred embodiment, the perforations in the orifice plate 110 are substantially circular in shape at the intersections of the holes with an upper surface of the orifice plate 110 and have a diameter in a range between about 4.63 microns and about 5.22 microns. Preferably, the piezoelectric actuator 79 is identical or similar to that found in commercially available electronic air freshening apparatus sold under the present assignee's WISP® trademark.

The piezoelectric element 80 is connected by wires 118 to a printed circuit board (PCB) 120 (FIGS. 2 and 3), discussed in greater detail hereinafter. The wires 118 supply an alternating electrical voltage produced by circuitry disposed on the PCB 120 to opposite sides of the piezoelectric actuator 80. A diameter of he actuator 80 alternately increases and decreases in size when alternating electrical voltages are applied to the piezoelectric actuator 80, thereby causing the orifice plate 110 to vibrate up and down due to the contact of the actuator 80 with the orifice plate 110. The orifice plate 110 is, in turn, in contact with fluid supplied by the wick 75. The up and down vibration of the orifice plate 110 causes liquid to be driven through the perforations or holes in the orifice plate 110 and the liquid is emitted upwardly in the form of aerosolized particles. The particles traverse an unobstructed interior 122 (FIG. 2) of the housing 22 and pass through the aperture 28 in the portion 24 of the housing 22.

The PCB 120 is mounted to a top surface 132 of the upper plate 42 by a pair of retention fingers 134 (FIGS. 2 and 3). Specifically, the PCB 120 is positioned between the retention fingers 134 and shoulders 136 disposed on inner surfaces 138 of one or more supports 140. As seen specifically in FIGS. 2 and 3, the PCB 120 includes a slide switch 148 having a slidable button 152 extending outwardly therefrom. The button 152 is moveable to one of three detent positions, which are discussed in greater detail hereinafter. Referring also to FIGS. 1 and 1A, a position selector 154 is moveable within a slot 155 and includes a yoke 156 that surrounds the button 152 on sides thereof to move the button 152 (the position selector 154 and the yoke 156 are not shown in FIG. 3). The position selector 154 is moveable to three selectable positions corresponding to the three detent positions of the button 152. Optionally, the selector 154 and the button 152 may be moveable to any number of selectable positions. The position selector 154 is preferably made of a light transmissive material, e.g., a translucent or transparent plastic such as clear or clarified polypropylene, polycarbonate, polyethylene, or any suitable plastic having a light transmission characteristic. As best seen in FIG. 1A, an LED 170 is supported by a bracket 172 extending upwardly from the upper base plate 42 and is aligned with and is disposed behind the selector 154 and is viewable therethrough at least from behind the device 20 when the selector 154 is moved to an on position (i.e., when the selector 154 is moved to two of the three detent positions of the button (152.). The LED 170 is connected by wires 174 to the PCB 120, wherein the PCB 120 controls illumination of the LED 170, as discussed in detail below. The position of the slide switch 148 is detected by circuitry mounted on the PCB 120 to control the operating mode and emission frequency of the diffusion device 20.

Figure 2A:
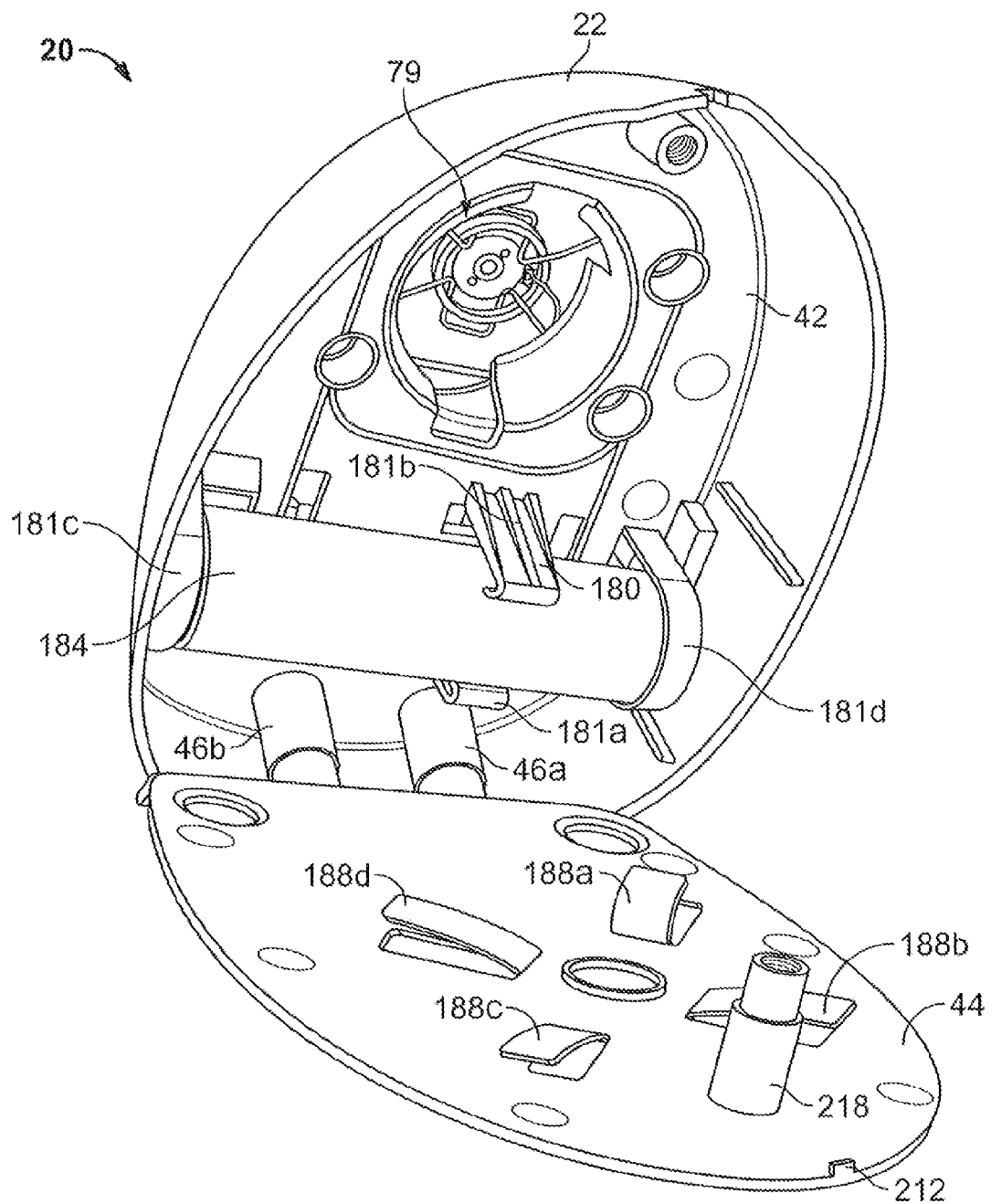
FIG. 2A is a lower isometric view of the embodiment of FIG. 1 illustrating the hinged base plate in an open position to reveal components therein.
Figure 6:
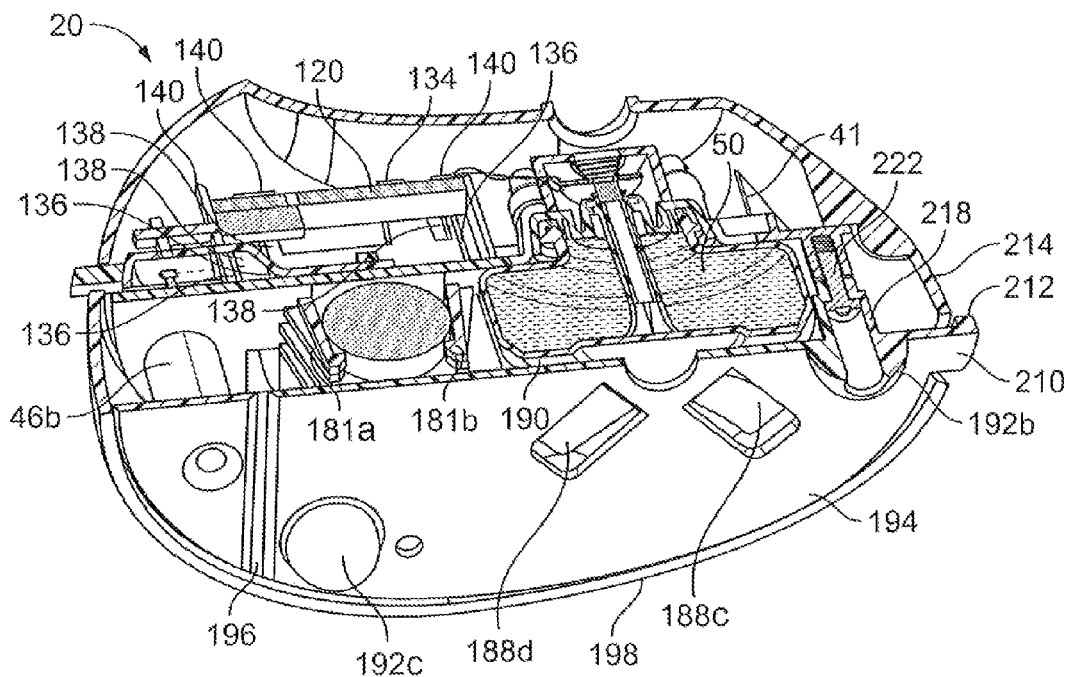
FIG. 6 is a bottom isometric view of the cross section shown in FIG. 2.

As seen in FIGS. 2, 2A, and 6, the upper plate 42 further includes a battery holder 180 including retention fingers 181a, 181b and end contact members 181c, 181d extending from a bottom surface 182 thereof. The battery holder 180 is adapted to receive a single 1.5 volt AA alkaline-manganese dioxide battery 184 and includes contacts for supplying an electrical voltage to the PCB 120. If desired, the single AA battery may be replaced by any number of other batteries or another power source.

Referring to FIGS. 2, 2A, and 6, the lower base plate 44 includes a plurality of flexible arms 188a-188d that taper upwardly from the lower base plate 44. The arms 188a-188d resiliently press against a bottom surface 190 of the replaceable fluid reservoir 50. Three support feet 192a-192c (FIGS. 2, 3, and 6) protrude downwardly from a bottom surface 194 of the lower base plate 44. The lower base plate 44 further includes a hinge 196 (FIGS. 2, 2A, and 6) comprising a thinned section disposed adjacent the support feet 192a, 192c. The hinge 196 defines a door 198 that can be pivoted downwardly away from the upper base plate 42 to provide access to an inside portion of the diffusion device 20. A first end 210 of the lower base plate 44 includes an upwardly extending flange 212 that abuts an outside surface 214 of the housing 22 when the door 198 is in a closed position as seen in FIG. 2. The flange 212 comprises a latch that engages an outer portion of the housing 22 to assist in holding the door 198 in a closed position.

A channel 216 extends through the support foot 192b and the lower plate 44 and extends to and through the upper base plate 42, in part being defined by a channel wall 218. An inner surface of the channel wall 218 includes a shouldered portion 219 (FIG. 2). A threaded bore 220 extends through the upper base plate 42 and is aligned with an end of the channel 216. A screw 222 is inserted into the channel 216 and is threaded into the bore 220 until a head of the screw 222 engages the shouldered position 219 to secure the door 198 in a closed position.

Figure 7:
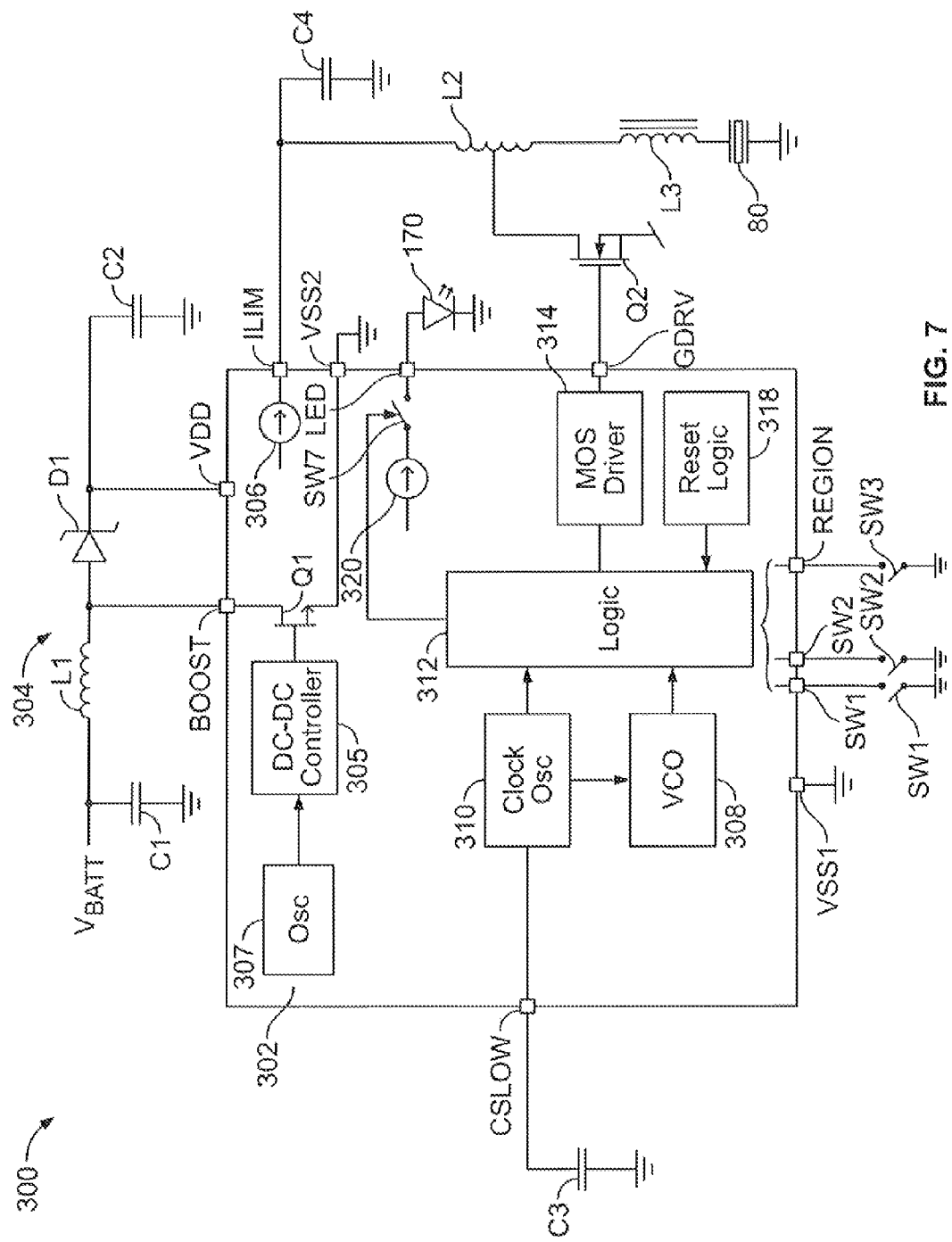
FIG. 7 is a combined block and schematic diagram of an exemplary circuit for controlling one or more components of the diffusion device of the present invention.

FIG. 7 illustrates circuitry 300 for operating the diffusion device 20. The circuitry 300 may include an application specific integrated circuit (ASIC) 302 manufactured by austriamicrosystems AG of Unterpremstaetten, Austria. Alternatively, the ASIC 302 may be replaced by a microprocessor, discrete circuit components, or a combination of any suitable devices. The circuitry 300 further includes a DC-DC boost converter 304 including capacitors C1 and C2, inductor L1, and Shottky diode D1 that, together with a DC-DC controller 305, an oscillator 307, and a transistor Q1 located on-board the ASIC 302, boost a 1.5 volt output of the battery 184 to provide a 3.3 volt nominal operational voltage to an input BOOST of the ASIC 302. In addition, a regulated voltage is developed at a junction between the Shottky diode D1 and the capacitor C2 and is delivered to a terminal VDD of the ASIC 302. The boost converter 304 starts up upon insertion of a battery with a minimum voltage of 1.20 volts. Once the ASIC 302 has properly started, the ASIC 302 continues to operate down to a minimum battery voltage of 0.9 volts. The oscillator 307 is controlled by on-chip circuitry to develop an oscillator signal sufficient to cause the DC-DC converter 304 to maintain the voltage delivered to the terminal VDD at the regulated value until the battery 184 discharges to a point at which such voltage cannot be maintained.

Ground potential is connected to input terminals VSS1 and VSS2. A terminal CSLOW is coupled by a capacitor C3 to ground. The ASIC 302 develops an output waveform $V_{GDRV}$ on a terminal GDRV, which is coupled by inductors L2 and L3 to the piezoelectric element 80 by a transistor Q2. The current delivered to the piezoelectric element 80 is maintained at a limited value as determined by a current source 306 following a part of he ASIC 302 and which is developed at an output terminal ILIM. The constant current course 306 charges the capacitor C4 at a level of approximately 3.3 milliamps while the voltage VDD is greater than 3 volts. When the voltage VDD drops below 3 volts, the constant current source 306 is switched off in a soft fashion.

A junction between the terminal ILIM and the inductor L2 is coupled by a capacitor C4 to ground. The output waveform $V_{GDRV}$ of the ASIC 302 is derived from a voltage controlled oscillator (VCO) 308, which is, in turn, responsive to the output of a clock oscillator 310. The frequency of the clock oscillator 310 is determined by the value of the capacitor C3. The VCO 308 utilizes an on-chip capacitor (not shown) and a charging/discharging bias current (that is also developed on-chip) to generate a control signal that is utilized by a logic block 312 and a driver block 314 to develop the output waveform $V_{GDRV}$. The logic block 312 comprises a frequency divider and a infinite state machine that controls the emission sequence in accordance with the positions of switches SW1, SW2, and SW3 that are coupled to corresponding terminals SW1, SW2, and REGION, respectively, of the ASIC 302.

Figure 8:
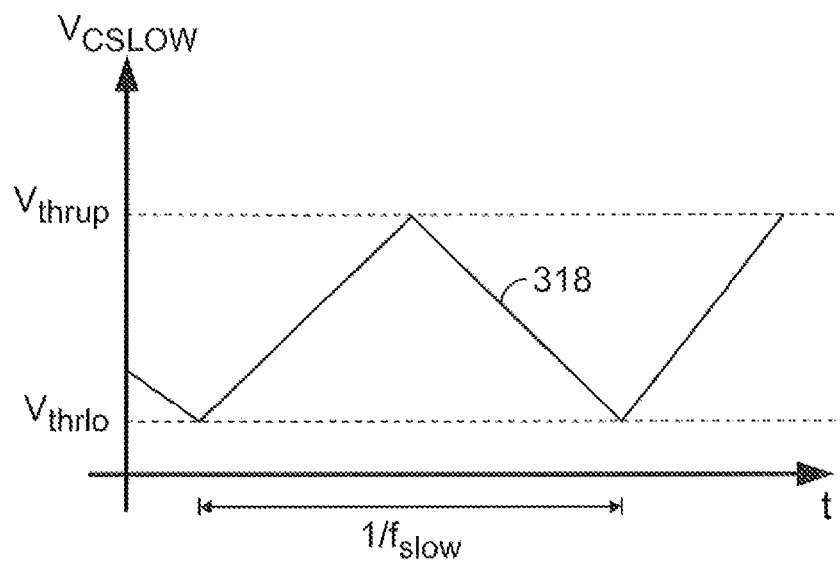
FIG. 8 is a waveform diagram illustrating a waveform $V_{CSLOW}$ developed by the circuit of FIG. 7.
Figure 9:
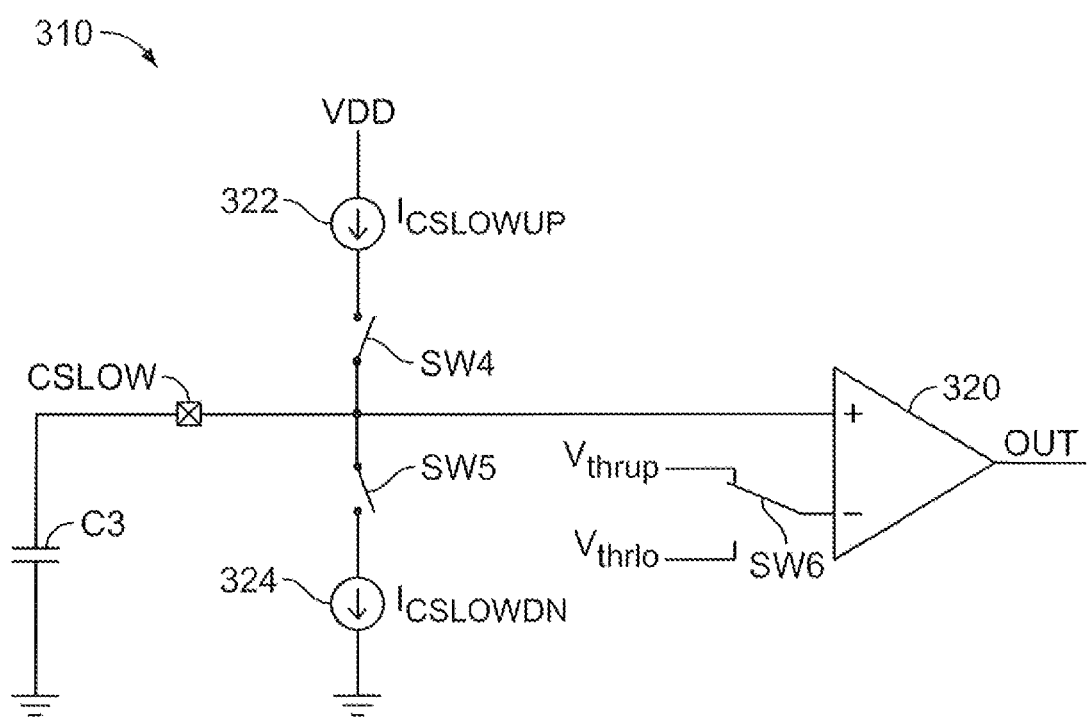
FIG. 9 is a circuit diagram functionally illustrating operation of the VCO 308 of FIG. 7.

The VCO 308 is operative during the time that emission is to occur (referred to hereinafter as an "emission sequence"), and is otherwise in an off state. A voltage $V_{CSLOW}$ developed across the capacitor C3 comprises a triangle voltage 318 illustrated in FIG. 8 having a period $1/f_{slow}$ and an amplitude that linearly varies between $V_{thrlo}$ and $V_{thrup}$. As seen in FIG. 9, the clock oscillator 310 is repeated by an operational amplifier 320 having a non-inverting input coupled to the terminal CSLOW, a pair of switches SW4 and SW5 that alternately connect current sources 322, 324 to the terminal CSLOW, and a further switch SW6 that alternately connects an inverting input of the operational amplifier 320 to voltage sources that develop the voltages $V_{thrlo}$ and $V_{thrup}$.

Figure 10:
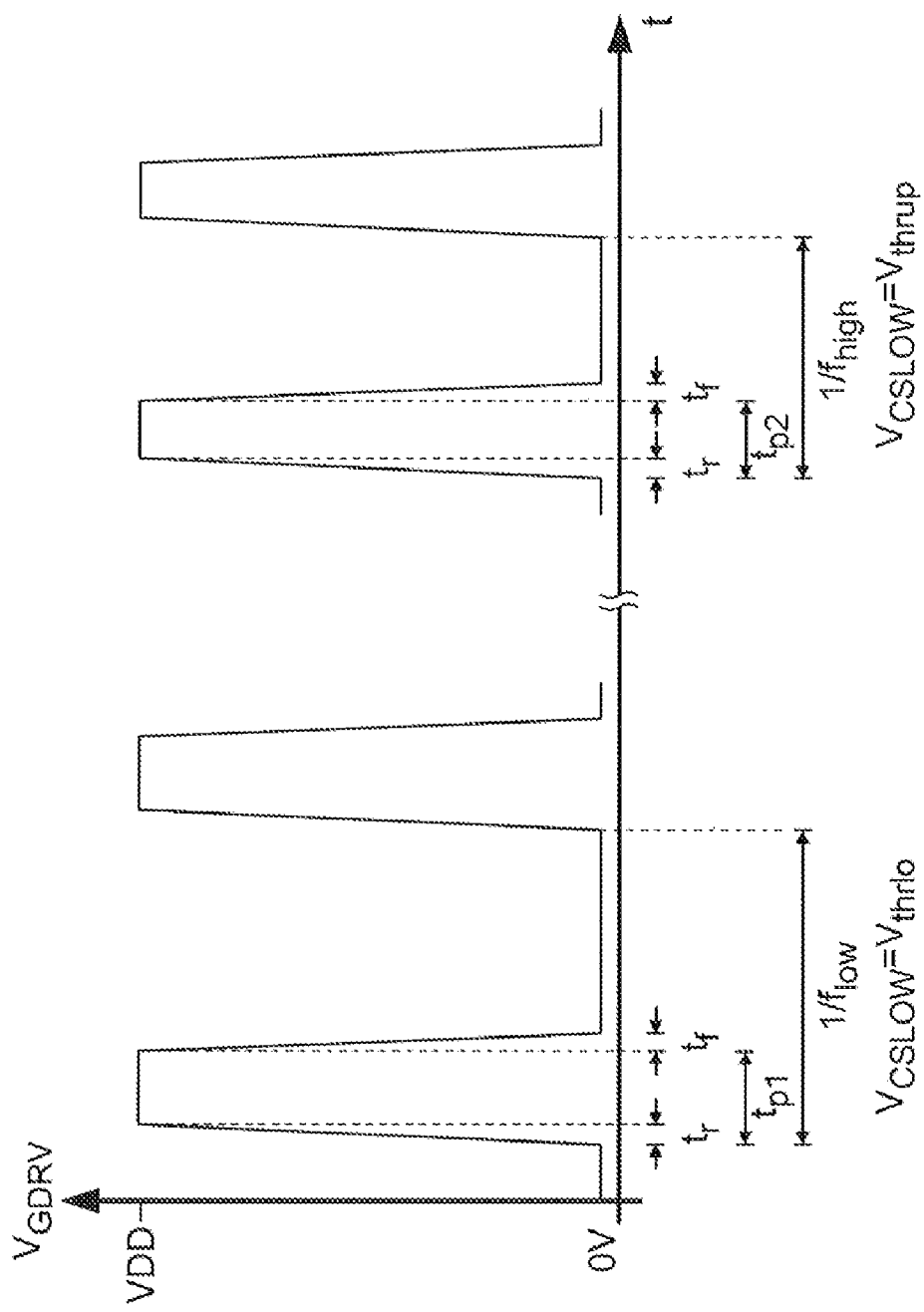
FIG. 10 is a waveform diagram illustrating a waveform $V_{GDRV}$ developed by the circuit of FIG. 7.

Referring next to FIG. 10, the drive voltage $V_{GDRV}$ is modulated between lower and upper frequency limits $f_{low}$ and $f_{high}$ during an emission sequence. The frequency is controlled by the waveform 318 illustrated in FIG. 8. The frequency range is selected to ensure that at some point during an emission sequence the piezoelectric element 80 is driven at a resonant frequency thereof. Specifically, the frequency range is selected to encompass the expected tolerance range of resonant frequencies of the piezoelectric elements that are intended to be driven by the ASIC 302. The frequency of $V_{GDRV}$ increases from the low limit to the high limit ad ramps back down to the lower limit multiple times during an emission sequence in accordance with the triangle waveform of 318.

Preferably, the ASIC 302 is placed into a reset state at power-up by a reset logic block 318 that is coupled to the logic block 312. The ASIC remains in the reset state for a predetermined period of time, following which a first emission sequence occurs according to the setting of the switches SW1-SW3.

The LED 170 is controlled by the logic block 312 to switch rapidly between on and off states in response to the operation of a switch SW7 that is controlled by the logic block 312. The switch SW7 alternate connects and disconnects a constant current source 320 to the LED 170 to cause the LED to appear to be continuously (or, optionally, intermittently) energized and which provides significant energy savings to minimize the demand on the battery 184. In accordance with a preferred embodiment, the logic block 312 operates the switch SW7 according to a modulation scheme such that the LED 170 is operated at 5% duty cycle at a frequency equal to $f_{low}/10$ hertz at a current that varies between 2.55 and 3.85 milliamps. Of course, any or all of these parameters may be varied, as desired, provided that the desired display condition (i.e., continuous or intermittent apparent illumination is realized. These particular recited parameters result in an average current draw of 160 microamperes, which is a sufficently small value to allow a single AA battery to be used and still achieve a useful battery lifetime. This need for only a single battery is a significant advantage over other devices that utilize an LED or other high energy utilization device, which typically require multiple batteries. In particular, the single AA battery is preferably capable of powering the device 20 for 10 hours a day for at least 40 days, and more preferably at least 45 days.

Figure 11:
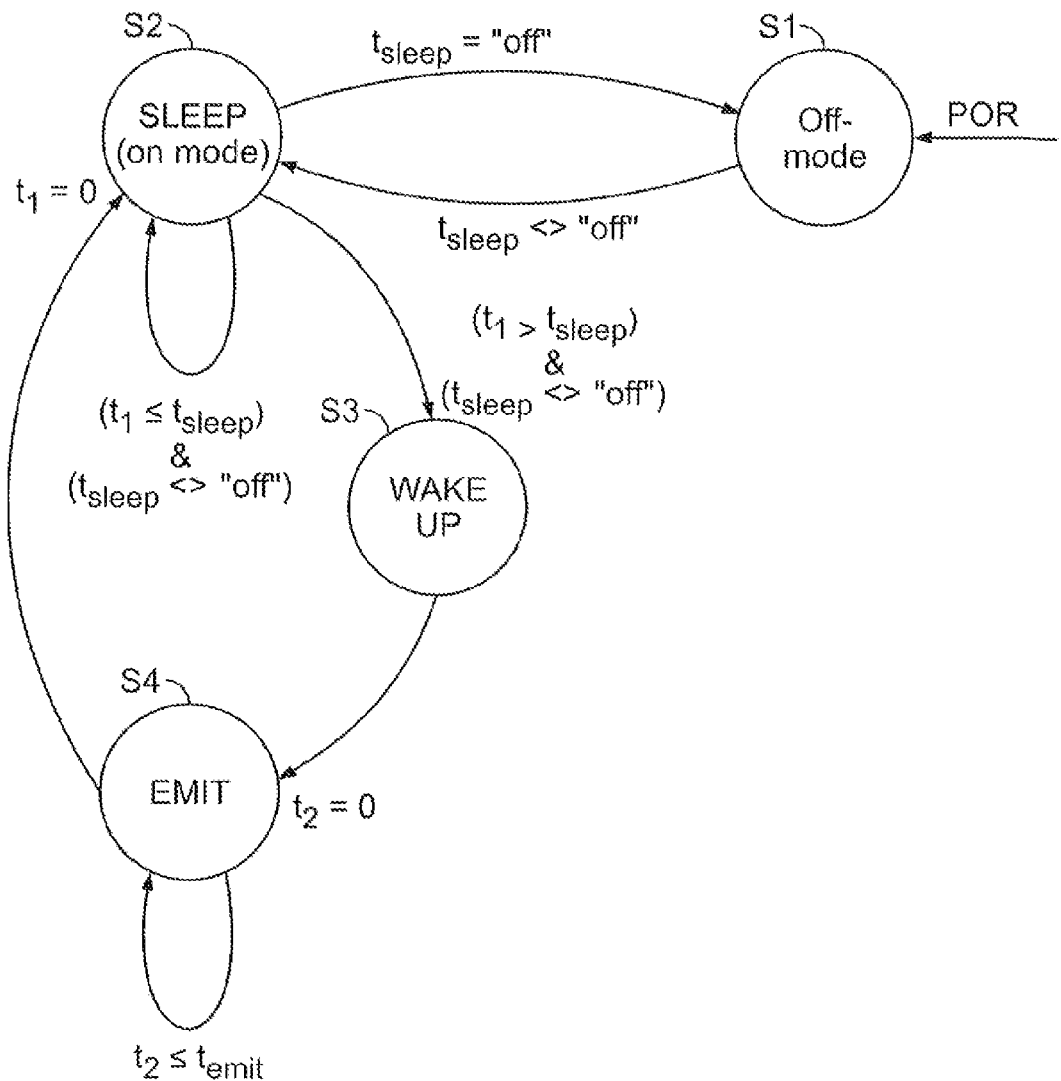
FIG. 11 is a state diagram illustrating operation of the logic block 312 of FIG. 7.

FIG. 11 is a state illustrating operation of the logic block 312 of FIG. 7. The logic block 312 is operable in one of four modes of operation comprising states S1, S2, S3, and S4. The state S1 comprises an off mode mode that is entered from a powered-down condition by generation of a power-on reset (POR) signal by the reset logic block 318 when the button 152 is moved to an on position while a battery 184 having a sufficient charge is in the device 20. During operation in the state S1, the LEDF 170 is de-energized and the VCO 308 is also de-energized so that no emission of volatile product is occurring. At this point, a pair of timers $t_1$ and $t_2$ are initialized and held at zero values. Independently of operation according to the state diagram of FIG. 11, the state of the switches SW1-SW3 are read to determine a value for a parameter $t_{sleep}$. The truth table for the switches SW1, SW2, and SW3 is as follows (a zero indicates a closed state of the corresponding switch while a one state indicates an open condition of such switch):

TABLE 1

| Parameter | SW1 | SW2 | SW3 | Sleep Time $t_{sleep}$ [seconds] (typical values) |
|---|---|---|---|---|
| $t_{off}$ | 0 | 0 | X | "off" |
| $t_{off}$ | 1 | 1 | X | "off" |
| $t_s 1$ | 0 | 1 | 1 | 7.2 |
| $t_s 2$ | 1 | 0 | 1 | 5.4 |

TABLE 1-continued

| Parameter | SW1 | SW2 | SW3 | Sleep Time $t_{sleep}$ [seconds] (typical values) |
|---|---|---|---|---|
| $t_s 3$ | 0 | 1 | 0 | 6.0 |
| $t_s 4$ | 1 | 0 | 0 | 4.5 |

As is evident from the foregoing, when the switches SW1 and SW2 are both in the same state, the parameter $t_{sleep}$ is set to an "off" value; otherwise, the parameter $t_{sleep}$ is set to one of four values $t_s 1$, $t_s 2$, $t_s 3$, or $t_s 4$. The values of $t_s 1$, $t_s 2$, $t_s 3$, and/or $t_s 4$ may be varied from those shown, as desired. The number of clock cycles $n_{sleep}$ is based upon the value $t_{sleep}$ that is selected by the switches SW1-SW3.

Referring again to FIG. 11, if the value of $t_{sleep}$ is not equal to the value "off," control passes to a state S2 comprising a sleep mode of operation. Immediately upon entry into the state S2, the timer $t_1$ is released to begin counting of clock pulses developed by the clock oscillator 310. Also during operation in the state S2, the VCO 308 is powered down so that the voltage $V_{GDRV}$ at the terminal GDRV is set to and maintained at a low state. Accordingly, no emission of volatile product occurs at this time. Further, the LED 170 is provided with current according to the operation of the logic block 312 as described above so that the LED 170 preferably appears to be continuously energized. Control remains in the state S2 as long as the value of $t_{sleep}$ is not equal to the value "off" and the timer $t_1$ has measured a time duration less than or equal to $t_{sleep}$. Eventually, control passes from the state S2 to the state S3 when the time $t_1$ has detected a time interval greater than $t_{sleep}$, provided that the value of $t_{sleep}$ has not been set equal to the "off" value at or prior to such time.

During operation in the state S3, the VCO 308 is powered and the voltage $V_{GDRV}$ is maintained at the lower level. Further, the logic circuit 312 senses the voltage at the terminal VDD to determine whether a 3.0 volt minimum has been developed at such terminal. If this is not found to be the case, such fact is noted by incrementing a register of the ASIC 302 (not shown). If the state S3 has been entered a particular consecutive number of time and VDD has been determined not to have reached the minimum 3.0 voltage value during any of these consecutive periods of time, then a low battery flag of the SCIC 302 is set, the LED 170 is de-energized to indicate that the device 20 is not operating, and the logic 312 establishes the voltage $V_{GDRV}$ at a high level, causing the transistor Q1 to turn on and increase the current drain on the battery. This last action, which may be undertaken when the voltage VDD has failed to reach the 3.0 volt threshold during 31 consecutive entries into the state S3, has the effect of preventing the battery from recovering and cycling in and out of a low battery condition.

If a determination is made that the voltage VDD has reached the 3.0 volt threshold during operation in the state S3, the LED 170 is preferably energized according to the scheme described above such that the LED 170 appears to be continuously energized. Control then passes from the state S3 to the state S4, whereupon the timer $t_2$ is released and counts clock pulses developed by the clock oscillator 310. Further, the logic block 312 develops the voltage $V_{GDRV}$ of FIG. 10 at the terminal GDRV until the register $t_2$ counts a particular number of clock pulses. This particular number may comprise, for example, 11 clock cycles corresponding to approximately 11 milliseconds. Also during operation in the state S4, the LED 170 is energized according to the scheme described above. At the end of the 11 millisecond emission sequence, control returns to the state S2, whereupon the timer $t_1$ is reset to zero and is released to accumulate clock pulses as described above.

Control passes from the state S2 to the state S1 when a determination is made that the value of $t_{sleep}$ has to be set equal to the "off" value.

The states of the switches SW1-SW3 are detected once every predetermined member of clock cycles by pulling the inputs SW1, SW2 and REGION up for a signal clock cycle and reading the inputs of the end of such clock cycle. The terminals SW1, SW2, and REGION are pulled down for a certain number of clock cycles between reading of the inputs, such as 127 clock cycles. The reading of the states of the switches SW1-SW3 occurs independently of the operational states of the logic block 312. Activating the pull-ups of the inputs SW1, SW2, and REGION for only one clock cycle out out of 128 cycles to accomplish reading reduces current consumption in the case where the one or more of the switches SW1-SW3 are closed so that the corresponding terminal SW1, SW2, and REGION is pulled down to a low voltage level.

In a preferred embodiment, the terminal REGION can either be wire bonded to the terminal VSS or may be left permanently open. In this fashion, the three-positionl switch 148 may be used having off, low, and high settings and which develops signals according to the truth label set forth above to accomplish this result. For example, the REGION terminal may be wire bonded to VSS if the device 20 is to be operated in a first region of the world or may be left open permanently if the device 20 is to be used in a different area of the work that, for example, permits a higher level of volatile active to be released into the atmosphere.

As should be evident from the foregoing, the logic block 312 preferably comprises the LED 170 to blink at 100 hertz and at a 5% duty cycle during on periods of the LED 170 when the diffusion device 20 is in a low or high switch setting and when the battery has sufficient voltage to drive the piezoelectric element 80. Also preferably, the logic block 312 de-energizes the LED 170 when the switch is in the off position or when the battery voltage drops such that VDD is less then 3.0 volts. Still further in accordance with the preferred embodiment, the LED 170 is placed behind the position selector 154 and the latter is fabricated of translucent or transparent material(s) so that the LED 170 is visible therethrough. Thus, a user is able to readily determine the operational status of the device 20.

Additional features of the device 20 include the use of a hinged bottom door with screw that enables the device to meet regulatory requirements for use with insecticides and/or insect repellents.

Also in accordance with the preferred embodiment, the diffusion device 20 and/or the fluid reservoir 50 may be modified so that the device 20 is capable of accepting only reservoirs 50 that contain a particular fluid and so that the reservoir 50 cannot be used in devices for which such reservoir 50 is not designed. Specifically, the lugs 74a, 74b may be lengthened in total by a distance of approximately 1 millimeter and the portion of the support chassis 40 may be modified to accept such lengthened lugs 74 as compared to similar diffusion devices that emit fragrances or other volatile liquids. The result of such modifications is that a reservoir 50 containing insecticide and/or insect or repellent cannot be used inside a similarly-designed fragrance dispenser. Conversely, a conventional reservoir having relatively shorter lugs 74 might be able in the device 20 or, conversely, the device 20 may be modified to prevent such use.

Still further in accordance with the preferred embodiment, the release rates for the device 20 are controlled to within the tight tolerances to satisfy regulatory requirements for use what insecticides and/or insect repellents. By controlling the range of diameters of the perforations in orifice plate 110 such that a hole diameter range of between about 4.63 microns and about 5.22 microns is imposed, unit-to-unit variability may be reduced to +/−30% or better. In fact, selecting an appropriate nominal perforation diameter in combination with a perforation diameter tolerance range and a formula of given viscosity and/or other characteristics can result in a precisely metered amount of volatile material per emission sequence. In addition, this would result in less of the dispensed material falling out and more of the dispensed material volatilizing at a faster rate due to the relative increase in surface to mass ratio yielding greater and faster effects on an insect. Perforation diameters in this range also result in lower relative variation in rates between devices 20 and thus a tighter range of dispensing rates.

The ASIC 302 is designed to provide emission sequences at approximately twice the frequency of known dispensing devices that utilize piezoelectric actuators. This increase in frequency enables use of relatively low vapor pressure solvents, thus lowering solvent losses when the device 20 is switched off. At the same time, release rates are sufficient to provide desirable efficacy and duration (e.g., similar to a 45 night liquid electric product).

If desired, the emission sequence and off times can be adjusted to ensure that battery life is synchronized with reservoir life so that both can be changed at the same time. Alternatively, one or both of the one and off times may be changed to avoid this synchronization.

According to a preferred embodiment, the reservoir 50 may be covered in a shrink wrap material to inexpensively meet regulatory requirements. Also, the reservoir 50 may be enclosed in a cardboard container that prevents photodegradation of the contents thereof.

INDUSTRIAL APPLICABILITY

Preferably, the volatile material stored in the reservoir 50 contains a solvent and one or more insecticide(s). The following attributes may be considered in selecting an insecticidal formula (i.e., solvent, insecticide(s), and percentage of the insecticide(s)) in combination with nominal perforation diameter and diameter tolerance (none of the attributes or examples presented herein should be considered limiting in any way):

TABLE 2

| No. | Attribute | Notes |
|---|---|---|
| 1 | The solvent (or solvent mixture) should not damage surfaces with nitrocellulose wooden finishes (most commonly found indoors and most susceptible to solvent damage). | Table 3 following demonstrates that alkanes cause the least damage to a nitrocellulose lacquer finish. |
| 2 | The solvent (or solvent mixture) preferably does not leave a substantial amount of on-volatile residue on the pump. Deposits may be expected to lead to inconsistent release rates from the product, especially when the product is not used continuously. | Table 4 following provides data on gum content on EXXSOL ® D95 and NORPAR ® 14. |
| 3 | The solvent (or solvent mixture) preferably has a sufficiently low evaporation rate to prevent substantial preferential loss of solvent. If preferential loss of solvent is | Table 5 following investigates the effect of boiling point on evaporation losses as |

TABLE 2-continued

| No. | Attribute | Notes |
|---|---|---|
| | minimal, the concentration of active remains predominantly unchanged and hence efficacy over the life of refill may not change substantially. | percentage of total weight loss. |
| 4 | The solvent (or solvent mixture) preferably has a maximum viscosity tailored to the characteristics of the pump (or a viscosity less than such maximum) to enable the pump to release the formula effectively. | Table 5 also demonstrates that the viscosity of the solvent may be ≦ about 4 cSt for the solvent to be effective in a piezoelectric device. |
| 5 | The solvent (or solvent mixture) preferably is substantially compatible with the insecticide(s) (this means that the insecticidal composition has good solubility and storage stability in the solvent). | Table 6 following shows storage stability data (54 degrees Celsius/2 wks, 40 degrees Celsius/3 months) indicating substantial stability of active in NORPAR ® 13. |
| 6 | Solvents with different boiling points can be blended to obtain desirable release rate characteristics. | Table 7 following shows release rate data of solvents with different boiling point ranges. Contrary to intuition (one would expect the high volatiles to escape at a fast rate leading to fractionation in the refill bottle and impact release rates), boiling point range did not impact release rates. |
| 7 | The orifice plate 110 preferably has hole diameters between about 4.63 microns and 5.22 microns. This leads to small droplet sizes (that leads to an improvement of efficacy* due to multiple factors) as well as reduced variability in release rates. | Table 8 following shows droplet size as a function of orifice plate hole diameter. |

(EXXSOL ® is a registered trademark of Exxon Mobil Corporation of Irving, Texas, for its brands of chemicals for use in the manufacture of polyolefins and halobutyls, chemicals for use as blowing agents in the manufacture of foam, and chemical solvents for use in the manufacture of adhesives, automotive fluids, cleaners, degreasers, coatings, paints, cosmetics, printing inks, and toiletries.)
(NORPAR ® is a registered trademark of Exxon Mobil Corporation of Irving, Texas, for its brand of fluid hydrocarbon solvents for general use in the industrial arts.)
*It is known that the molecular form of the insecticide is much more effective than when the insecticide is in the droplet form. Smaller droplets evaporate faster (because of larger surface area per unit volume of the droplet) and more completely (because they suspend longer in the air due to their small size).

Attribute 1. Damage to Surfaces

The effect of various solvents was explored by placing a droplet of the solvent on a clear nitrocellulose lacquer finish for 15 minutes. The droplet was then wiped dry and the damage caused by the solvent to the surface finish noted:

TABLE 3

| Solvent | Type | Observation |
|---|---|---|
| Acetone | Ketone | Lacquer finish completely dissolved |
| N-Methyl Pyrrolidone | Nitrogen Compound | Lacquer finish completely dissolved |
| Ethylene Glycol Butyl Ether | Alcohol | Lacquer finish partially dissolved |
| DOWANOL ® DPM | Alcohol | Lacquer finish partially dissolved |
| DOWANOL ® PnP | Alcohol | Lacquer finish partially dissolved |
| n-Heptane | Alkane | No impact on lacquer finish |
| ISOPAR ® E | Alkane | No impact on lacquer finish |
| Ethanol | Alcohol | No impact on lacquer finish |
| Propylene Glycol | Polyhydric alcohol | No impact on lacquer finish |
| Water | | No impact on lacquer finish |
| Diethylene Glycol Butyl Ether | Alcohol | No impact on lacquer finish |
| Isopropyl Myristate | | No impact on lacquer finish |
| 1-Propanol | Alcohol | No impact on lacquer finish |
| NORPAR ® 13 | Alkane | No impact on lacquer finish |
| NORPAR ® 14 | Alkane | No impact on lacquer finish |
| NORPAR ® 15 | Alkane | No impact on lacquer finish |

(DOWANOL ® is a registered trademark of Dow Chemical Company of Midland, Michigan, for its brand of industrial chemical polyoxyalkylene compositions useful as; leather dying formulations; as solvents in dyes, wood stains, textile printing pastes and dyes, nail polish, lacquers, and inks; as both solvents and coupling agents in textile lubricants, in metal working lubricants, and in agricultural chemical products; in rust removers, internal combustion engine cleaners, metal parts cleaners, dry cleaning soaps, and spotting fluids; as cellophane adhesive solvents, agricultural chemical solvents, and rosin soldering flux solvents; as solvents for drug and antibiotic manufacture, safety glass manufacture, and for mineral oil dewaxing; in low temperature antifreezes, hydraulic brake fluid formulations, whitewall tire cleaners, crank case decontaminants, and sizes for fibers; and as perfume fixatives, aerosol vapor pressure modifiers, lubricating oil additives, and cleaning fluids for enameled surfaces.)
(ISOPAR ® is a registered trademark of Exxon Mobil Corporation of Irving, Texas, for its brand of fluid hydrocarbon solvents of petroleum origin for general use in the industrial arts.)

Conclusions: None of the alkanes caused damage to the nitrocellulose lacquer finish. Some alcohols, glycol ethers, ketones, and nitrogen compounds caused damage. Hence, alkanes (examples include ISOPAR®'s, EXXSOL®'s, hexane, heptane, dodecane, tetradecane, etc.) are preferred. From the foregoing, the presence of an active material in solvent is not expected to alter the results of damage caused to the nitrocellulose lacquer finish as weight percent of the solvent present in such solutions is far greater than the weight percent of the active material.

Although alkanes are preferred, the solvent may alternatively comprise alcohols, glycol ethers, ketones, nitrogen compounds, and mixtures of any or all of the foregoing.

Attribute 2: Gum Content

It is desirable to minimize gum content to minimize the build-up of residue on the orifice plate 110 over time. Tests using the ASTM D-381 testing protocol on EXXSOL® D95 solvent and one lot to NORPAR® 13 solvent yielded the following results:

TABLE 4

| Solvent | Gum Content |
|---|---|
| EXXSOL ® D95 | 3.6 mg |
| NORPAR ® 13 | <1 mg |

Conclusion: NORPAR® solvents are preferred due to their low gum content, although EXXSOL® solvents might be used.

Attribute 3: Effect of Solvent Volatility on Evaporative Losses and Release Rates A highly permeable wick is used in the diffusion device 20 to ensure easy and effective transfer of the liquid from the tip of the wick to the orifice plate 110. In addition, the plug and wick holder 72 that is fitted to reservoir 50 includes two small orifices to enable equilibration of pressure between the headspace in the reservoir and the surrounding atmosphere. These design factors lead to slow evaporation of the solvent regardless of whether the device 20 is switched on or off. Solvents with high volatility tend to evaporate more rapidly leading to concentration of the insecticide in the reservoir 50. This increases the viscosity of the formula and slows down the overall release rates, leading to a negative impact on product performance. The following Table 5** shows evaporative losses and the release rate of formulations of various solvents over the life of a refill bottle.

than or substantially equal to about 3 cSt is more referred as this enables the insecticidal concentration(s) to be kept below 100%.

Conclusion: Viscosity of the solvent preferably less than or substantially equal to about 4 centistokes (cSt) at 25 degrees Celsius and more preferably less than or substantially equal to about 3 cSt at 25 degrees C. This conclusion is true for 8.0 wt %/wt % Transfluthrin in solvent, as well as for pure solvent. In other words, this conclusion can be expected to hold true for any insecticide as long as it is present in a concentration low

TABLE 5

| Solvent | Mid point of the boiling point of the solvent (deg F.) | Viscosity of Solvent (cSt at 25 deg. C.) | With Pure Solvent | | | With 8.0 wt %/wt % Transfluthrin in Solvent | | |
|---|---|---|---|---|---|---|---|---|
| | | | Release Rate in High Setting (mg/hr) | Evaporation Loss (mg/hr) | Evaporation Loss as Percent of Release Rate | Release Rate in High Setting (mg/hr) | Evaporation Loss (mg/hr) | Evaporation Loss as Percent of Release Rate |
| NORPAR ® 14 | 475 | 2.8 | 9.4 | 0.46 | 5.0% | 9.3 | 0.25 | 2.7% |
| EXXSOL ® D110 | 499 | 3.5 | 6.6 | 0.28 | 4.3% | 5.6 | 0.24 | 4.3% |
| EXXSOL ® D130 | 566.5 | 6.9 | 0.7 | 0.08 | 11.7% | 1.2 | 0.06 | 4.8% |
| NORPAR ® 13 | 450 | 2.4 | 10.2 | 1.02 | 10.0% | 9.0 | 0.47 | 5.2% |
| EXXSOL ® D95 | 448 | 2.6 | 9.6 | 0.56 | 5.9% | 11.1 | 0.92 | 8.3% |
| EXXSOL ® D220-230 | 442.4 | 2.44 | 7.2 | 1.17 | 16.2% | 11.7 | 1.01 | 8.6% |
| EXXSOL ® D80 | 429.5 | 2.2 | 14.5 | 1.78 | 12.3% | 14.7 | 2.36 | 16.1% |
| ISOPAR ® M | 461 | 3.8 | 7.4 | 1.04 | 14.0% | 6.2 | 1.03 | 16.6% |
| ISOPAR ® L | 387.5 | 2 | 21.0 | 6.42 | 30.5% | 18.5 | 6.55 | 35.4% |
| PROGLYDE ® DMM | 347 | 1.1 | 24.0 | 8.29 | 34.5% | 27.1 | 11.53 | 42.5% |
| DOWANOL ® DPM | 374 | 3.9 | 6.7 | 2.49 | 37.3% | 4.6 | 2.17 | 47.1% |
| DOWANOL ® PnP | 300.2 | 2.7 | 25.3 | 9.73 | 38.4% | 22.0 | 16.05 | 73.1% |

(PROGLYDE ® is a registered trademark of Dow Chemical Company of Midland, Michigan, for its brand of glycol ethers for use as solvents in the coatings, agriculture, and mining industries.)
**Release rates and evaporation losses reported here were averaged over 3 repetitions. For each repetition, release rates were determined by measuring weight loss when the unit was left in the ON position in high switch setting for an average of 13 hours. Evaporation rates were determined for each repetition by measuring weight loss when the unit was left in OFF switch position for an average of 30 hours.

Conclusion: The percentage of evaporation losses from 8.0 wt %/wt % Transfluthrin in the solvent formula are strongly correlated to a mid point of a boiling point of the solvent in degrees Fahrenheit as shown in the table above. When the mid point of the boiling point of the solvent is greater than 400 degrees Fahrenheit, the percentage of evaporation losses stay below 20% and hence these solvents are preferred. As insecticides are not very volatile, presence of an insecticide is expected to further reduce the evaporation rates from these insecticidal solations and hence, for insecticidal formulation, solvents with a mid point of a boiling point range of 400 degrees Fahrenheit or greater will limit the evaporation losses to less than 20% of the release rate.

Attribute 4: Effect of Viscosity on Release Rates

Referring again to Table 5, release rates of 8.0 wt %/wt % Transfluthrin in solvent are strongly correlated to viscosity of solvent. A solvent viscosity of less than or substantially equal to about 4 centistokes (cSt) at 25 degrees Celsius is preferred as release rates stay above 5 mg/hr. Release rates lower than 5 mg/hr require much higher concentration of insecticide (higher insecticidal concentrations lead to thickening of the formula which may become unacceptable to delivery via piezoelectric delivery systems). A solvent viscosity of less enough so that the viscosity of the solvent is not significantly altered. Therefore, other insecticides such as Metofluthrin, Etoc, Pynamin Forte, Pyrethum Extract, Esbiothrin, Vaporthrin, etc. may also be used.

Attribute 5: Stability of Insecticide in Solvent

Stability data determined using analytical tools are given below:

TABLE 6A

| Formula | % Transfluthrin at the start | % Transfluthrin after storing the sample for 2 weeks at 54 deg, C. |
|---|---|---|
| 8.0 wt %/wt % Transfluthrin in NORPAR ® 13 | 8.3 wt %/wt % | 83 wt %/wt % |

TABLE 6B

| Formula | % Metofluthrin at the start | % Metofluthrin after storing the sample for 5 weeks at room temperature |
|---|---|---|
| 2.5 wt %/wt % Metofluthrin in NORPAR ® 14 | 2.5 wt %/wt % | 2.49 wt %/wt % |

Conclusion: Transfluthrin and Metofluthrin are stable in hydrocarbon solvents.

Attribute 6: Effect of Boiling Point Range on Release Rates

The effect of solvents with different boiling point ranges on release rates were studied and the results are show in the following Table 7:

TABLE 7

| Solvent | Boiling Point Range | Difference between Low and High Boiling Points | Average Release Rate during 1-5 days (mg/hr) | Average Release Rate during 6-10 days (mg/hr) | Average Release Rate during 11-14 days (mg/hr) | Residual Liquid (gm) |
|---|---|---|---|---|---|---|
| PROGLYDE ® DMM | 347° F. | 0° F. | 23.3 | 23.0 | 15.7 | Zero |
| DOWANOL ® PnP | 300.2° F. | 0° F. | 19.1 | 18.0 | 10.0 | Zero |
| NORPAR ® 14 | 466-484° F. | 18° F. | 10.4 | 10.7 | 10.2 | 4.4 |
| EXXSOL ® D95 | 435-461° F. | 26° F. | 8.3 | 8.8 | 9.1 | 4.5 |
| ISOPAR ® L | 370-405° F. | 35° F. | 10.0 | 12.4 | 15.8 | 2.9 |
| NORPAR ® 13 | 432-468° F. | 36° F. | 11.8 | 12.5 | 12.1 | 3.7 |
| EXXSOL ® D80 | 406-453° F. | 47° F. | 12.8 | 13.2 | 12.9 | 3.6 |
| ISOPAR ® M | 433-489° F. | 55° F. | 5.4 | 5.9 | 6.7 | 4.6 |
| EXXSOL ® D-110 | 480-514° F. | 34° F. | 6.6 | 6.9 | 6.8 | 4.9 |
| EXXSOL ® D-95 + EXXSOL ® D-110 (50:50) | 435-514° F. | 79° F. | 8.2 | 9.2 | 9.1 | 4.4 |
| ISOPAR ® L + ISOPAR ® M (50:50) | 370-489° F. | 119° F. | 9.6 | 9.4 | 10.1 | 3.0 |

Note:
Release rates on each day were determined by measuring the total amount lost from the unit when the switch is in high setting for an average period of 7.1 hours.

Conclusion: The range of boiling points does not impact release rates. This facilitates blending of solvents with different viscosities to obtain desirable release rate characteristics.

Attribute 7: Effect of Orifice Plate Hole Diameter on Droplet Size

The following Table 8 shows the mean particle size (measured in Malvern particle sizes using the Malvern particle method where the $D(v, 0.5)$ statistic means that 50% of the mass or volume of the particles have particle sizes below $D(v, 0.5)$ and the remaining 50% have particle sizes above $D(v, 0.5)$ and the $D(v, 0.9)$ statistic means that 90% of the mass or volume of the particles have particle sizes below $D(v, 0.9)$ and the remaining 10% have particle sizes are $D(v, 0.9)$) emitted from pumps having orifice plates with different hole diameters.

TABLE 8

| Hole diameter in microns | $D(v, 0.5)$ in microns | $D(v, 0.9)$ in microns |
|---|---|---|
| 4.66 | 3.22 | 5.68 |
| 4.92 | 3.28 | 5.73 |
| 5.19 | 3.39 | 9.06 |
| 5.51 | 3.50 | 8.08 |
| 6.71 | 5.66 | 14.06 |

CONCLUSION

Pumps with smaller hole diameters delver smaller droplets that tend to stay in the air longer and evaporate more completely. Larger droplets tend to fall down and create a residue on the diffusion device 20 as well as around the diffusion device 20, especially when the diffusion device 20 is used in a draft-free and/or relatively enclosed area. The orifice plate 110 preferably has hold diameters between about 4.63 microns and about 5.22 microns. Although 8.0 wt %/wt % Transfluthrin in NORPAR® 13 was used to measure particle sizes, these particle sizes were measured close to the orifice plate 110, and hence the particle sizes are expected to be independent of the insecticide.

Exemplary Formula

Based on the foregoing test results, one preferred embodiment comprises a composition preferably containing between about 0.25 wt %/wt % and about 60 wt %/wt % Transfluthrin, more preferably between about 2.0 wt %/wt % and about 40.0 wt %/wt % Transfluthrin, and most preferably about 8.0 wt %/wt % Transfluthrin in NORPAR® 13 utilized in a diffusion device 20 having an orifice plate 110 with 84 perforations of nominal hole diameter of between about 4.63 microns and about 5.22 microns and using the device 20 described hereinabove and shown in the attached FIGS.

Another embodiment comprises a composition preferably containing between about 0.05% wt %/wt % and about 12.0 wt %/wt % Metofluthrin, more preferably between about 0.5 wt %/wt % and about 8.0 wt %/wt % Metofluthrin, and most preferably about 2.5 wt %/wt % Metofluthrin in NORPAR® 14 utilized in diffusion device 20 having an orifice plate 110 with 84 perforations of nominal hole diameter of between about 4.63 microns and about 5.22 microns and using the device 20 described hereinabove and shown in the attached FIGS.

Numerous modifications to the present invention will be apparent to those skilled in the art in view of the foregoing description. Accordingly, this description is to be construed as illustrative only and is presented for the purpose of enabling those skilled in the art to make and use the invention and to teach the best mode of carrying out same. The exclusive rights to all modifications which come within the scope of the appended claims are reserved.

We claim:

1. A diffusion device, comprising:

a housing having a battery disposed therein and adapted to receive a replaceable fluid reservoir for holding a fluid, the fluid reservoir including a wick for movement of the fluid to a discharge end thereof;

a piezoelectric element energized by the battery for vibrating a perforated orifice plate disposed adjacent the discharge end of the wick, wherein the piezoelectric element develops vibratory movement to pump the fluid from the discharge end through the perforated discharge plate and into the atmosphere; and a control circuit and a light emitting diode ("LED") disposed in the housing, wherein the control circuit rapidly switches the LED between on and off states in response to the operation of a switch that alternately connects and disconnects a current source to the LED when the piezoelectric element is energized and a voltage developed by the control circuit is above 3.0 volts such that the battery is prevented from cycling in and out of a low battery condition.

2. The diffusion device of claim 1, wherein the LED is disposed behind a translucent selector that is carried by the housing and wherein the selector is movable into three selectable positions corresponding to different modes of operation.

3. The diffusion device of claim 1, wherein the piezoelectric element is energized during an emission sequence for about eleven milliseconds to periodically discharge contents of the container to the atmosphere.

4. The diffusion device of claim 1, in combination with a replaceable fluid container containing an insecticide and wherein the battery has a useful life substantially equal to a useful life of the replaceable fluid container.

5. The diffusion device of claim 1, wherein a hinged door is disposed adjacent a bottom portion of the housing and wherein the door is secured to the housing by a screw.

6. The diffusion device of claim 1, wherein the fluid in the fluid reservoir comprises an insecticide in an alkane-based solvent.

7. The diffusion device of claim 6, wherein the alkane-based solvent comprises primarily tridecane and tetradecane.

8. The diffusion device of claim 7, wherein the insecticide comprises about 8.0 wt %/wt % Transflutbrin.

9. The diffusion device of claim 7, wherein the insecticide comprises about 2.5 wt %/wt % Metoflutlirin.

10. The diffusion device of claim 1, wherein the current source is a constant current source and the LED is rapidly switched between on and off states at about 100 hertz.

11. The diffusion device of claim 1, wherein the control circuit implements a modulation scheme that operates the LED at a 5% duty cycle at a current that varies between about 2.55 milliamps and about 3.85 milliamps.

12. The diffusion device of claim 11, wherein the modulation scheme results in an average current draw of about 160 microamperes.

13. A diffusion device, comprising:

a housing adapted to receive a replaceable fluid reservoir for holding a fluid, the fluid reservoir including a wick for movement of the fluid to a discharge end thereof;

a piezoelectric element for vibrating a perforated orifice plate disposed adjacent the discharge end of the wick, wherein the piezoelectric element develops vibratory movement to pump the fluid from the discharge end through the perforated discharge plate and into the atmosphere;

a control circuit and a light emitting diode ("TED") disposed in the housing, wherein the control circuit rapidly switches the LED between on and off states in response to the operation of a switch that alternately connects and disconnects a constant current source to the LED; and only one 1.5 volt AA battery coupled to the control circuit and disposed within the housing, wherein the only one battery and the control circuit drive the piezoelectric element and the LED such that the piezoelectric element is periodically operated to dispense fluid from the device for 10 hours a day for at least 45 days, and wherein the control circuit ranidly switches the LED between on and off states at a particular frequency when the piezoelectric element isenergized and a voltage developed by avoltage boost circuit is above 3.0 volts such that the battery is prevented from cycling in and out of a low battery condition.

14. The diffusion device of claim 13, wherein the control circuit implements a modulation scheme that operates the LED at a 5% duty cycle at a current that varies between about 2.55 milliamps and about 3.85 milliamps.

15. The diffusion device of claim 14, wherein the modulation scheme results in an average current draw of about 160 microamperes.

16. The diffusion device of claim 13, wherein the fluid in the fluid reservoir comprises an insecticide in an alkane-based solvent.

17. The diffusion device of claim 16, wherein the alkane-based solvent comprises primarily tridecane and tetradecane.

18. The diffusion device of claim 17, wherein the insecticide is selected from the group consisting of about 8.0 wt % wt % Transfluthrin and about 2.5 wt %/wt % Metofluthrin.

19. The diffusion device of claim 13, wherein the orifice plate has 84 holes with a nominal hole size between about 4.63 microns and about 5.22 microns.

* * * * *

UNITED STATES PATENT AND TRADEMARK OFFICE
CERTIFICATE OF CORRECTION

PATENT NO.         : 7,455,245 B2
APPLICATION NO.    : 11/457728
DATED              : November 25, 2008
INVENTOR(S)        : Gene Sipinski et al.

It is certified that error appears in the above-identified patent and that said Letters Patent is hereby corrected as shown below:

Column 17, Line 35: replace "Transflutbrin" with --Transfluthrin--

Column 17, Line 37: replace "Metoflutlirin" with --Metofluthrin--

Column 18, Line 3: replace "fluidreservoir" with --fluid reservoir--

Column 18, Line 23: replace "ranidly" with --rapidly--

Column 18, Line 25: replace "isenergized" with --is energized--

Column 18, Line 26: replace "avoltage" with --a voltage--

Column 18, Line 43-44: replace "8.0 wt % wt %" with --8.0 wt %/wt %--

Signed and Sealed this

Twenty-fourth Day of March, 2009

JOHN DOLL
*Acting Director of the United States Patent and Trademark Office*